United States Patent [19]
DellaPenna et al.

[11] Patent Number: 6,127,179
[45] Date of Patent: Oct. 3, 2000

[54] GENE PROMOTER FOR TOMATO FRUIT

[76] Inventors: Dean DellaPenna, 4135 Longknife Rd., Reno, Nev. 89509; Colin F. Watson, 2701 N. Avenida Empalme, Tucson, Ariz. 85715

[21] Appl. No.: 08/632,806

[22] Filed: Apr. 17, 1996

[51] Int. Cl.[7] .............................. C12N 5/14; C12N 15/82; C12N 15/11; A01H 5/10
[52] U.S. Cl. .......................... 435/419; 435/411; 536/24.1; 800/218; 800/317.4
[58] Field of Search .................................. 536/24.1, 23.6; 435/410, 411, 419; 800/205, 250, 298, 317.4

[56] References Cited

PUBLICATIONS

Bird, C.R. et al. Plant Molecular Biology, vol. 11, pp. 651–662, 1988.
Zheng, L. et al. The Plant Cell, vol. 4, pp. 1147–1156, Sep. 1992.

*Primary Examiner*—Mary E. Mosher
*Attorney, Agent, or Firm*—Quarles & Brady LLP

[57] ABSTRACT

The tomato polygalacturonase (PG) β-subunit promoter has been isolated and sequenced. The promoter can be used to make gene constructs including a protein-coding nucleotide sequence not natively associated with the promoter and a sufficient portion of the promoter such that the portion actuates the preferential expression of the protein-coding nucleotide sequence in tomato tissue. While other β-subunit genes are found in tomato, the tomato fruit PG β-subunit promoter is particularly useful as a both tissue specific and developmentally regulated promoter.

6 Claims, 3 Drawing Sheets

1. Amplify to make new SmaI site

2. Cut with SmaI and PmeI, purify fragment.

~170 bp PCR product

3. Digest pβSUB1/RV clone with PmeI and SmaI to remove all sequences downstream of PmeI site
4. Ligate 170 bp PmeI/SmaI PCR product to PmeI/SmaI cut clone, sequence with T7 primer to confirm orientation and fidelity of sequence.
5. Cut new clone with HindIII and SmaI, ligate into transformation vector cut with same enzymes.

FIG 3

GENE PROMOTER FOR TOMATO FRUIT

FIELD OF THE INVENTION

The present invention relates to the general technology of plant genetic engineering and, in particular, to the identification of tissue-specific promoters and the use of these promoters to create novel genetically transformed plants.

BACKGROUND OF THE INVENTION

High quality ripe fruit results from a number of coordinated biochemical, metabolic, and storage changes which occur not only during ripening but also during fruit development prior to ripening. Collectively, these changes determine the final quantity and quality of the fruit. Some of the more commercially important traits include the import of sugars (principally sucrose) into the developing fruit from photosynthetically active portions of the plant and incorporation of this sugar into starch, accumulation of various organic acids in specific ratios, modifications of pigments involved in coloring of the fruit and changes in fungicidal or insecticidal compounds.

Polygalacturonase

In recent years *Lycopersicon esculentum*, the cultivated tomato, has become a popular system for studying fruit ripening. Tomato fruit ripening is characterized by a series of coordinated biochemical and physiological changes within the various subcellular compartments of the fruit tissue. These changes collectively contribute to the overall quality of the ripe fruit. The most obvious of the changes are alterations in fruit color, flavor, texture and resistance to certain pathogens.

One biochemical change in ripening fruit is the depolymerization and solubilization of cell wall polyuronides by the ripening-induced cell wall degrading enzyme, polygalacturonase (PG). PG activity increases dramatically during the ripening of many fruits, including tomato, and is the primary enzymic activity responsible for cell wall polyuronide degradation during fruit ripening. Reviewed in Giovannoni, et al, 1991 *Ann. Rev. Hortic Sci*: 67–103.

PG activity isolated from ripe tomato fruit is due to the presence of three structurally and immunologically-related isoforms of PG. These isoforms are termed PG1, PG2A and PG2B. (Ali, et al. *Aust. J. Plant Physiol*. 9:171, 1982). The PG2A and PG2B isoforms (45 and 46 kDa, respectively) appear well after the onset of ripening and are each composed of a single catalytic PG polypeptide differing only in degree of glycosylation. Because of the physical and biochemical similarity of PG2A and PG2B, the two isoforms shall be treated herein as a single isoform activity (the PG2 activity).

The PG1 isoform (approximately 100 kDa) is the first isoform to appear, at the onset of ripening, and is a heterodimer composed of the single catalytic PG2 polypeptide (either PG2A or PG2B) tightly associated with an ancillary cell wall glycoprotein, the PG β-subunit. The formation of PG1 by association of the PG2 polypeptide with the PG β-subunit protein alters both the biochemical and enzymic properties of the associated catalytic PG2 protein. The isoelectric point and pH optimum of PG1 are both a full unit lower than those of PG2. PG1 is more thermo-stable than PG2. PG1 retains complete activity after heating for 5 minutes at 65° C., a treatment that completely inactivates PG2.

In recent years, CDNA clones for the catalytic PG2 polypeptide have been identified and used to examine in detail the regulation of PG gene expression in wild-type and mutant tomato fruit (DellaPenna, et al, *Proc. Natl. Acad. Sci. USA* 83:6420 (1986). Analysis of PG2 genomic and CDNA clones has revealed that the catalytic PG polypeptide is encoded by a single gene which is transcriptionally activated at the onset of wild-type fruit ripening (DellaPenna et al, *Plant Physiol*. 90:1372 (1989). PG2 mRNA is synthesized de novo during the ripening of wild-type fruit and accumulates to high levels, accounting for greater than 1% of the mRNA mass. Ripening-impaired mutants of tomato, which are inhibited in many ripening processes including PG2 expression, have greatly reduced levels of PG2 mRNA. The severe reduction in steady-state PG mRNA levels in the mutant genotypes is due to greatly reduced transcriptional activity of the PG gene (DellaPenna, et al, 1989, supra)

The PG β-subunit has also been studied. The levels of PG β-subunit increase approximately 4-fold during fruit ripening (Pressey, R., *Eur. J. Biochem*. 144:217–221 (1984)) and apparently determine the amount of PG1 produced during tomato ripening. Therefore, as PG β-subunit levels are depleted (by formation of PG1), the timing of appearance of the PG2 isoform is also controlled.

While it is clear from in vitro studies that PG1 and PG2 differ in their biochemical properties, the physiological significance of the isoforms and the role of the PG β-subunit protein remains uncertain. From a physiological point of view, it seems likely that a cell wall enzyme like PG might be localized or its activity restricted to specific regions of the cell wall by association with an adhesion or localizing factor, such as the PG β-subunit protein. Recent results in transgenic systems have also suggested that PG1 may be the physiologically active isoform in vivo with regard to pectin degradation, presumably due to its association with the PG β-subunit protein.

Pectolytic enzymes, such as PG, may have a role in plant pathogen interactions. Pathogen-derived pectolytic enzymes are thought to be important components of the mechanism by which pathogens penetrate and colonize plant tissues. Preliminary results from recently completed experiments have suggested that PG induction in transgenic mutant fruit increases colonization of the fruit by *Alternaria alternata*, a common late-season pathogen of wild-type tomato fruit to which mutant fruit are normally resistant. The apparent conferral of pathogen sensitivity to mutant fruit by the specific induction of PG expression suggests that increasing PG activity during fruit ripening may play an important role in altering the susceptibility of the fruit to pathogens.

Both classical breeding and genetic manipulations have been used to improve specific aspects of fruit quality. In recent years a number of genetic manipulations have been performed to modify specific ripening aspects of tomato fruit, often with commercially useful results. Such molecular approaches have definite advantages over classical breeding. The most obvious advantages are the accelerated development of genetically engineered varieties with enhanced traits, and the highly directed nature of the process. That is, specific biochemical steps carried out by proteins produced by single genes or small related gene families, can be targeted for modification by overexpressing the particular gene involved in the target step, thereby "enhancing or accelerating" the targeted cellular process. Conversely, by inhibiting the expression of a gene or gene family a biochemical process can be reduced or inhibited. Such approaches can very specifically modify a trait in an already existing, commercially useful plant without affecting other desired traits.

The expression of plant genes has been successfully modified by the following methods: overexpression of genes/proteins, antisense or cosuppression to inhibit gene expression, or transposon disruption of genes, which also inhibits expression of a particular gene. The first three methods (overexpression, antisense inhibition and cosuppression) rely on the directed expression of a specific gene construct at developmental and/or tissue specific stages of the plant's lifecycle where the process of interest is to be modified.

Gene expression is better altered by using developmental and tissue specific promoters to target and restrict the modifications of the process of interest to the tissues and/or developmental times in the plant lifecycle which will be least detrimental and most commercially beneficial to the overall growth and development of the plant. Promoters are DNA elements that direct the transcription of RNA in cells. Together with other regulatory elements that specify tissue and temporal specificity of gene expression, promoters control the development of organisms. However, this approach depends on the availability of a promoter specific enough to limit the expression of the transgene to the organ and developmental stage of interest, while simultaneously allowing expression at a high enough level to effectively modify the target gene in these tissues. What is needed is a promoter that will allow the targeting of chimeric gene expression to developing tomato fruit.

SUMMARY OF THE INVENTION

The present invention is summarized in that a fruit ripening developmentally regulated promoter has been identified in the promoter for the fruit β-subunit of polygalacturonase (PG).

The present invention also includes a gene construct comprising the promoter portion of SEQ ID NO:7 and a protein-coding nucleotide sequence that is not natively associated with the promoter portion of SEQ ID NO:7. By "protein coding sequence" we mean a sequence that encodes at least a portion of a protein and is in either the sense or antisense direction.

In another embodiment, the present invention is a gene construct comprising a protein-coding nucleotide sequence not natively associated with SEQ ID NO:7 and a sufficient portion of SEQ ID NO:7 such that the portion actuates the preferential and developmentally regulated expression of the protein-coding nucleotide sequence in tomato tissue. By "expression" we mean to include DNA sequences expressed into RNA and/or into protein.

In another embodiment, the present invention is a gene construct comprising a protein-coding nucleotide sequence not natively associated with SEQ ID NO:7 and a promoter sequence sufficiently homologous to SEQ ID NO:7 such that the sequence provides preferential expression in tomato tissue.

It is an object of the present invention to provide a promoter useful in gene expression.

It is another object of the present invention to provide a promoter capable of providing preferential expression in tomato tissue.

It is another object of the present invention to provide SEQ ID NO:7.

It is another object of the present invention to provide a promoter sequence isolated from a PG1 β-subunit gene.

It is another object of the present invention to provide a sufficient portion of SEQ ID NO:7 such that preferential expression in tissue is obtained.

It is an advantage of the present invention that a transgenic plant may be created in which the transgene is expressed preferentially in tissue.

Other objects, features and advantages of the present invention will become apparent after examination of the specification, claims and drawings.

DETAILED DESCRIPTION OF THE INVENTION

In accordance with the present invention a new promoter element useful in creating transgenic plants is described. This promoter is from the fruit β-subunit of polygalacturonase (PG) from tomato. Specifically, the promoter is from the tomato gene here designated fruit PG β-subunit, or β-subunit, or βSUB1, to distinguish from the homologous β-subunit genes found to be expressed in other tissues. This promoter provides tissue-preferential, and developmentally regulated, expression of transgenes whose expression it regulates in transgenic plants. This promoter drives expression most abundantly in fruit, with also some lower expression level in flower.

The sequence of the tomato fruit PG β-subunit promoter is set forth in SEQ ID NO:7 below. A fruit specific promoter is thus available, i.e. containing either SEQ ID NO:7 or a portion or version of SEQ ID NO:7 sufficient to effect preferential expression of a transgene in plant fruit cells. The present invention is also a gene construct containing a promoter sequence isolated from the tomato fruit PG1 β-subunit gene, a gene expressed preferentially at high levels only in developing (green) tomato fruit, not in ripening tomato fruit, and at extremely low levels, if at all, in other tissues and organs of the plant.

A fruit specific, developmentally regulated promoter, such as that of the present invention, can control the expression of target genes which affect the quality of developing fruit without affecting the ripening process. Examples of such target genes include genes responsible for sugar or starch metabolism, source sink relation, organic acid balance, flavor components, pathogen resistance, soluble solids, and water/pH relations. This promoter exhibits both high expression and high specificity, suggesting significant value for these and similar objectives in transgenic plants.

The β-subunit promoter region resides on a 2.8 kb DNA fragment, identified as a part of the 3.2 kb genomic fragment set forth as SEQ ID NQ:7. That fragment contains all sequences sufficient to confer tissue specific expression when connected to a protein-encoding nucleotide sequence. All or part of the first 2644 base pairs of SEQ ID NO:7 may be used to direct the expression of foreign or endogenous genes in the sense orientation, or in the antisense orientation, for overexpression or cosuppression. The genes driven by the β-subunit promoter can be plant genes, specific fruit genes, or heterologous genes the expression of which is desired in plant fruit. This tomato promoter will be effective in other fruit-bearing plants as well.

To investigate native PG β-subunit expression characteristics, the expression patterns of β-subunit and PG2 were analyzed during wild-type tomato fruit development and in the pleiotropic ripening mutant rin (ripening-inhibitor), in which many aspects of ripening are inhibited, including PG2 expression. Northern and Western analysis was conducted to track the temporal regulation of the two native genes β-subunit and PG2 were found to differ dramatically in their temporal regulation during wild-type fruit development. β-subunit mRNA is detectable as early as 10 DAP (days after pollination) and increases gradually during development to its highest level at 30 DAP, just prior to the onset of ripening. During the following 5-day period, ripening is initiated and β-subunit mRNA decreases below detectable limits, while PG2 MRNA increases to its highest level. In non-ripening rin fruit, the β-subunit expression pattern was similar to the wild-type, indicating that there is no coupling or repression due to PG2 expression. This demonstrates that the PG β-subunit promoter is thus regulated by other tissue specific or developmental cues.

Using ethylene production as a marker, it was found that β-subunit and PG2 expression overlap slightly early in ripening. The progress of ripening was staged by measuring endogenous $C_2H_4$ production rates of individual fruit. Protein and RNA were isolated from the same tissue. Northern blot analysis of total RNA probed sequentially with $^{32}$P-labeled cDNA clones showed that PG2 protein is not detected until β-subunit mRNA levels decrease. Again, in the non-ripening mutant rin, the β-subunit expression pattern was similar to wild-type, despite an absence of PG2 expression. Ethylene treatment of wild-type and rin fruit did not significantly affect β-subunit expression.

These combined results suggest that β-subunit expression is independent of both ethylene and PG2 expression during fruit development, and thus regulated primarily by tissue specific or developmental cues. One likely explanation for the near complete temporal separation of β-subunit and PG2 expression is that β-subunit expression occurs early in fruit development to allow transport, attachment and localization of the β-subunit to specific regions of the cell wall. When the catalytic PG2 polypeptides are then expressed and secreted at the onset of ripening, they associate with the β-subunit at its targeted location in the cell wall rather than in transit.

β-subunit and PGase Expression in Other Tissues

To investigate tissue specificity, an analysis of similar genes in other tissues was undertaken. Northern analysis revealed that β-subunit mRNA could be detected in wild-type tomato root, leaf and flower tissues. Though expressed at much lower levels, the non-fruit β-subunit mRNA was identical in size to that in fruit.

Immunoblot analysis conducted with β-subunit antisera indicated a protein identical in size to the fruit β-subunit was also present in cell wall protein extracts of roots, leaves and flowers. The amount of protein detected was highest in floral tissue (~10% of fruit levels), while root tissue contained the lowest amount and a second fainter, larger band was also detected in root and leaf tissues. Developmental studies of floral tissues indicated the β-subunit antigen was present at all stages. Cell wall proteins from developing flowers were analyzed for both β-subunit and PG2 antigens. A second larger protein was also consistently detected at the 5 mm bud stage and beyond and decreased in size transiently during pollination (flower 2 stage). Surprisingly, western analysis of the same extracts with tomato fruit PG2 antibody detected a protein that was identical in size to tomato fruit PG2 and specifically expressed at the 5 mm and flower 1 stage, just prior to pollination and the decrease in size of the larger β-subunit antigen. The expression of proteins in floral tissues immunologically related to fruit PG2 and β-subunit suggests that an association of catalytic PGases and "β-subunit-like" proteins may also occur in this tissue.

Tissue Specific β-Subunit Expression in Floral Tissues

Floral tissues were analyzed in more detail to determine if β-subunit expression was constitutive or specific tissue. The former result would imply a structural role for the protein while the latter might support a role in regulating or targeting PG activity.

Western analysis of dissected flower parts demonstrated that expression of the immunologically detectable β-subunit antigens is largely restricted to stigma/style tissue and anthers/pollen. Their absence from ovary tissue is particularly noteworthy as the fertilized ovary gives rise to the fruit, a tissue where the fruit β-subunit is highly expressed in a developmentally regulated fashion. Stigma/style tissue exclusively contains the larger β-subunit antigen at a very high level, while two different sized β-subunit proteins are produced at lower levels in anthers/pollen.

In fruit tissue, β-subunit and PG2 expression are temporally separated during development. The results suggest a similar situation may occur in floral tissues, where PGases are largely restricted to pollen, while production of "β-subunit-like" proteins occurs at its highest level in stigma/style tissues. Stage 3 (fully opened) flowers were collected, dissected, and cell wall proteins (5 ugm) from the indicated organs were isolated and analyzed for β-subunit antigen. A high level of expression was detected in stigma/style and anthers/pollen and restriction of the larger antigen to stigma/style tissues. Such data argues an analogous functional role for "β-subunit-like" proteins in regulating or targeting PG activity in floral tissues, potentially to activate or target pollen produced PGases during growth of the pollen tube through the transmitting tissue of the style. Arguably, fruit and non-fruit β-subunit proteins perform similar functions, namely to immobilize, regulate or activate PG polypeptides in cell walls.

Gene Construct

The present invention enables the promoter sequence or subsequence to be combined with a protein-coding sequence in a gene construct. Commonly used methods of molecular biology well-known to those of skill in the art may be used to manipulate the DNA sequence.

By "gene construct" we mean any of a variety of ways of combining the promoter sequence with the protein-encoding sequence in a manner that operably connects the promoter sequence with the protein-encoding sequence. Typically, the promoter sequence will be 5' or "upstream" of the protein-encoding sequence.

For example, these two sequences may be combined together on a plasmid or bacterial vector or they can be assembled in vitro. Other functional sequences, such as secretion signals, polyadenylation and termination sequences, may be added to the gene construct. Alternatively, the protein-coding and promoter sequences may be combined together with only other needed functional sequences and used without a vector.

By "protein encoding sequence" we mean any nucleotide sequence capable of expression at the mRNA level. The mRNA may in turn be expressed as a protein or not. The protein encoding sequence may be in either the sense or antisense orientation. The antisense orientation would be useful to express antisense mRNA.

A suitable protein encoding sequence will not be associated with the promoter sequence in nature. For example, because the β-subunit protein coding sequence is naturally associated with SEQ ID NO:7, the β-subunit protein coding sequence in its native form is not a suitable protein encoding sequence.

SEQ ID NO:7 and Variants SEQ ID NO:7 is set forth below. SEQ ID NO:7 set forth the sequence of a 3.2 kb genomic clone including the promoter region, contained in base pairs 1–2644, as well as the 5' region of the fruit β-subunit coding region, beginning with the ATG at base 2645. There are several methods commonly known to those of skill in the art of molecular biology of obtaining this sequence. For example, one may create nucleic acid probes from the known sequence and use these probes to screen a tomato genomic library to obtain the entire sequence. Alternatively, one may synthetically create the sequence. One could also isolate the β-subunit protein, raise monoclonal or polyclonal antisera and probe a cDNA expression library. Once one had obtained the β-subunit cDNA, one can screen a genomic library for the promoter sequence. One could also isolate the protein, obtain a portion of the primary amino acid sequence and design degenerate enthetic oligonucleotide probes.

The Examples below disclose that SEQ ID NO:7 is sufficient to confer preferential expression of a protein encoding sequence in tomato tissue. However, we envision that the promoter region of bases 1–2644 SEQ ID NO:7 could be further truncated (for example, truncations could be made from either end of the promoter sequence), and still confer the same properties, because that sequence contains the transcription activators, but also contains other DNA not necessary for promoter activity. One skilled in the art of molecular biology would be able to take SEQ ID NO:7 and perform deletional analysis experiments to determine what portion of SEQ ID NO:7 is essential to confer tissue-specific expression. One could create a genetic construct with the candidate deletion mutations and a protein-encoding sequence and perform experiments with transgenic plants as described below in the Examples. Occurrence of the test protein sequence preferentially in tomato tissue indicates a successful deletion mutant. In this manner, and although such procedures would be tedious, one of ordinary skill in the art could determine which parts of SEQ ID NO:7 are essential for tissue-specific transcription.

In addition, it is well known that copies of genes vary from individual to individual, or variety to variety, within a species. Such variations are referred to here as allelic variations. Therefore, while there is certainly a β-subunit PG promoter in every tomato plant, that subunit may or may not have a sequence which is identical at each nucleotide to SEQ ID NO:7. Such allelic variations to SEQ ID:7 as may exist would not compromise the ability such a variation would have to confer preferential expression of a protein encoding sequence in tomato tissue, in exactly the same manner as does SEQ ID NO:7.

One skilled in the art of molecular biology would appreciate that minor deletion, addition and mutations may not change the attributes of SEQ ID NO:7. Many of the nucleotides of SEQ ID NO:7 are probably not essential for its unique function. To determine whether or not an altered sequence has sufficient homology with SEQ ID NO:7 to function identically, one would simply create the candidate mutation, deletion or alteration and create a gene construct including the altered sequence and a protein-encoding sequence. This gene construct could be tested as described below in the Examples for the occurrence of the test protein predominantly in tomato tillues in a transgenic plant.

The present invention is also a gene construct containing a promoter sequence isolated from β-subunit gene. By a "β-subunit gene" we mean a gene containing a sequence encoding the β-subunit protein.

EXAMPLES

Creation of β-subunit cDNA Clones

A CDNA library was prepared with RNA obtained from mature green tomato with a commercially available kit (Stratagene, LaJolla, Calif.). Mature fruit tissue was collected from greenhouse grown tomato plants and frozen with liquid nitrogen. Total RNA was extracted via the following method: Ten grams of frozen tissue was ground to a powder in liquid nitrogen with a mortar and pestle and homogenized with a polytron in 20 ml of lysis buffer [8 M guanidine thiocyanate, 10 mM EDTA, 300 mM Tris-Hcl (pH 7.6), 8% b-mercaptoethanol].

Following centrifugation at 3,000 g for 10 minutes, the supernatant was filtered through miracloth and extracted twice with phenol/chloroform and once with chloroform. RNA was ethanol precipitated and the resulting pellet was washed with 3.0 M sodium acetate (pH 5.5), then dissolved in 10 mM Tris, pH 7.6; 1 mM EDTA; 1% SDS and reprecipitated with 2.5 M LiCl (Sambook, et al, *Molecular Cloning Manual*, Cold Spring Harbor, 1989). Total RNA was subjected to poly A+ selection as described (DellaPenna, 1986 supra).

This cDNA library was screened with probes prepared from peptide fragments of PG. The fragments were obtained in the following way: Ripe pericarp tissue was homogenized in ice-cold distilled $H_2O$ at a ratio of 1 kg fruit to 1 liter water and the resulting slurry adjusted to pH 3.0. Cell debris was pelleted by centrifugation at 10,000 g for 20 minutes, resuspended in one half volume of cold $H_2O$ at pH 3.0 and repelleted. The cell debris pellet was resuspended in cold buffer contained 50 mM sodium acetate, 1.25 M NaCl (pH 6.0) and stirred for at least one hour at 4° C. The extract was centrifuged at 10,000 g for 20 minutes and proteins in the supernatant were precipitated by the addition of ammonium sulfate to 70% saturation. After centrifugation, the resulting protein pellet was resuspended in 0.125 M sodium acetate (pH 6.0) and dialyzed extensively against the same buffer. The dialyzed extract was then clarified by centrifugation and applied to a CM-Sepharose column equilibrated with 0.125 M sodium acetate (pH 6.0). Bound proteins were eluted by a two step gradient of 0.45 M sodium acetate (pH 6.0) and 1.0 M sodium acetate (pH 6.0). PG2 A and B eluted with 0.45 M sodium acetate while PG1 eluted with 1.0 M sodium acetate.

The 1.0 M sodium acetate eluent was concentrated by ultrafiltration, dialyzed against Concanavalin A (Con-A) buffer [500 mM NaCl, 50 mM sodium acetate, 1 mM calcium acetate, 1 mM manganese sulfate (pH6.0)] and further purified by Con-A chromatography as previously described (DellaPenna, 1986 supra). PG1-containing fractions were concentrated by ultrafiltration, dialyzed against 50 mM phosphate, 200 mM NaCl, 0.1 mM DDT (pH6.0) and further purified by Mono S FPLC chromatography, Pogson et al, *Aust. J. Plant Phys.* 18:65–79 (1991).

The subunits of PG1 were separated and isolated as described (Pogson et al., 1991 supra). PG1 purification and separation of PG2 and the β-subunit protein were followed by SDS-PAGE. Electrophoretic blotting, and detection methods for the catalytic PG polypeptide were performed as described previously (DellaPenna et al., 1986, supra). PG1 and PG2 levels during extraction and purification were determined by heat inactivation (Tucker et al., *Eur. J. Biochem.* 115:87–90, 1981) and activity staining of protein extracts separated by non-denaturing PAGE (DellaPenna, 1987 supra).

N-terminal sequence analysis of the purified β-subunit was performed with a Beckman 890M gas phase sequenator. Internal β-subunit proteolytic fragments were generated by digestion with Lys-C and Glu-C endoproteases following instructions supplied by the manufacturer (Promega, Madison, Wis.). The resulting proteolytic fragments were resolved by SDS-PAGE, blotted to PVDF membranes and directly sequenced.

Two internal peptide fragments were of interest. The amino acid sequence of the Lys-C peptide was: NH$_2$-Asn-Gly-Asn-Gly-Ala-Asn-Gly-Gln-[?]-Val (SEQ ID NO: 1). The amino acid sequence of the Glu-C peptide was: NH$_2$-Ala-Asn-Ala-Gly-Asp-Gln-Tyr (SEQ ID NO: 2). The underlined portion of these sequences indicates the sequence from which a nucleotide primer was constructed. These nucleotide primers are presented at SEQ ID NO: 3 (for the Lys-C primer) and 4 (for the Glu-C primer).

These degenerate oligonucleotides were used for library screening and PCR-based MOPAC generation of cDNA probes. One microgram of poly (A) +RNA from immature green, mature green, turning and fully ripe tomato pericarp tissues was used in PCR-based MOPAC reactions. A Not I primer-adaptor (Promega, Madison, Wis.) was used as a primer for first strand cDNA synthesis. Subsequent PCR amplification cycles utilized a Not I adaptor as the 3' primer and a degenerate 5' primer (SEQ ID NO: 4), derived from the Glu-C β-subunit protease fragment. Amplified products were electrophoresed, blotted to nylon membranes and probed with a second degenerate oligonucleotide (SEQ ID NO: 3) derived from the Lys-C β-subunit protease fragment. The Lys-C primer recognized a 1.3 kb product generated in the MOPAC reactions. This 1.3 kb product was recovered and amplified by PCR using the Lys-C primer (5'-end) and the Not I adaptor (3'-end). This second 1.25 kb MOPAC-derived PCR product was used in conjunction with degenerate oligonucleotides for library screening and Northern analysis. Oligonucleotide 5'-end labelling land random primer DNA labelling were performed following the manufacturer's protocol (BRL, Gaithersburg, Md.).

The cDNA library contained 1.0×10$^7$ individual recombinants before amplification. For primary screening, replica nitrocellose filters (25,000 pfu/plate) were probed with the degenerate 17-mer Lys-C oligonucleotide described above. Prehybridization was carried out for 4 hours at 37° C. in a solution of 6×SSC; 1×Denhardt's solution; 0.5% SDS; 0.05% sodium pyrophosphate; 100 ug/ml denatured salmon sperm DNA. Hybridization was carried out overnight at 37° C. in 6×SSC; 1×Denhardt's solution; 20 ug/ml tRNA; 0.05% sodium pyrophosphate. Following hybridization, the filters were washed twice for 5 minutes at room temperature and twice at 37° C. for 30 minutes in 5×SSC; 0.05% sodium pyrophosphate. A final wash was performed in 5×SSC; 0.05% sodium pyrophosphate at 40° C. for 10 minutes. The filters were exposed overnight with intensifying screens at −80° C.

Further rounds of screening were performed at low density using the PCR-generated MOPAC cDNA fragment (described above), the Glu-C oligonucleotide and a degenerate N-terminal oligonucleotide [5'-AT(AG) TCX CC(AG) CT(GA) TG(CT) TT(CT) TC (SEQ ID NO: 5)] derived from the N-terminal protein sequence. Hybridization conditions for these oligonucleotides were as described above. Hybridization conditions used with the MOPAC-generated cDNA fragments were as described by Sambook et al 1989, (supra). Following plaque purification, plasmids were rescued by in vivo excision, following the manufacture's protocol (Stratagene). Double-stranded DNA sequencing was performed.

Figure 1:
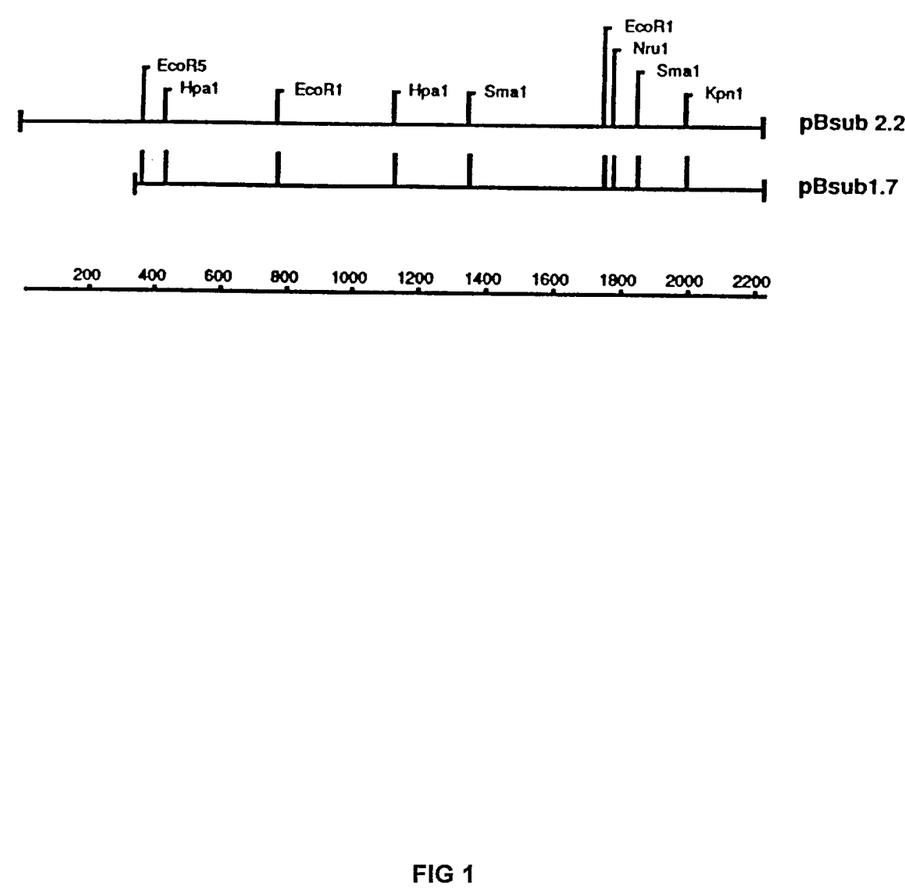
FIG. 1 is a restriction enzyme map of polygalacturonase β-subunit cDNA clones pBsub 2.2 and pBsub 1.7.

All the β-subunit clones we obtained have the restriction pattern illustrated in FIG. 1. We have sequenced two β-subunit cDNA clones and fragments of 11 others. SEQ ID NO: 6 is the consensus DNA sequence we obtained from the clones. A poly-(A) tail of 35 residues was found at the end of the cDNA but has been removed from SEQ ID NO: 6.

Isolation and Analysis of β-subunit Genomic Clones

Clones from an available VFNT Cherry tomato genomic library (courtesy of Dr. Robert Fischer) were isolated and analyzed using the β-subunit cDNA as a hybridization probe. To date the tomato variety Ailsa Craig has been used exclusively in the studies, however, the genetic background of VFNT and Ailsa Craig is very similar. This fact was confirmed by the identical results obtained from extensive southern and PCR analysis of genomic DNA from the two varieties which indicates the number and organization of β-subunit genes is conserved between the two varieties. Southern analysis of the four isolated genomic clones using fruit β-subunit cDNA subfragments and oligonucleotides indicated that the β-subunit genes can be classified into two groups, βSUB1 and βSUB2. All four clones hybridized with 5' and 3' fruit β-subunit cDNA probes and appeared to contain complete genes. βSUB1 encoded a complete fruit β-subunit gene including several kb of upstream and 3' downstream sequences. The βSUB2 clones hybridize only to 2 of 6 oligonucleotides derived from fruit β-subunit CDNA sequence; they are overlapping clones representing a second related β-subunit gene, βSUB2.

Figure 2:
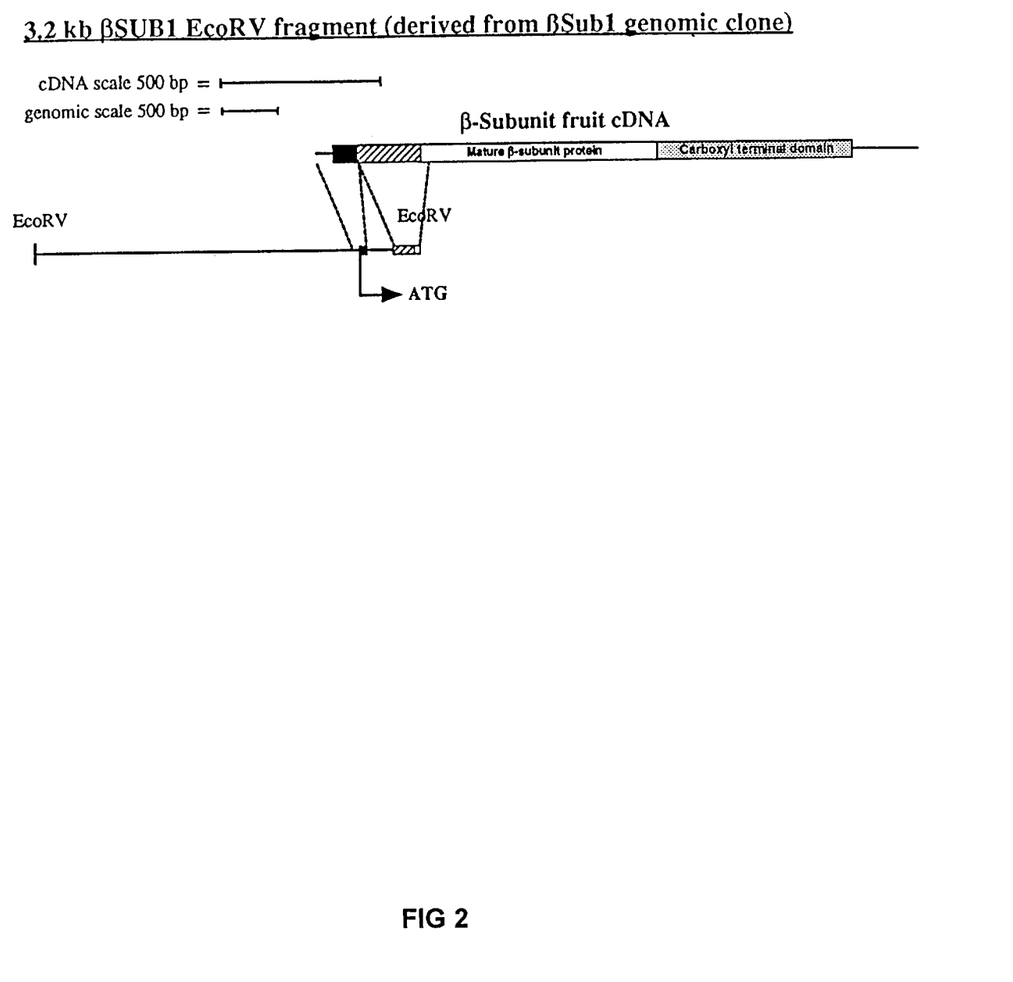
FIG. 2 illustrates a β-subunit genomic map including the subclone βSUB 1.

Gene fragments of βSUBS and βSUB2 were subcloned into pBluescript KS phagemid and sequenced. Sequencing confirmed that the 3.5 kb EcoRV subclone of βSUB1 shown in FIG. 2 contains >500 bp of coding region identical to the fruit β-subunit CDNA sequence and at about 2.8 kb of upstream promoter region. That promoter sequence is now identified as bases 1–2644 of SEQ ID NO:7. The 3.5 kb subclone of β-SUB1 shown in FIG. 2 encodes the fruit β-subunit cDNA. An approximate 10 kb subclone of a β-SUB2 was also obtained. Subsequently, it was learned that the β-SUB2 gene was not expressed in fruit, although it is a β-subunit type gene. The promoter from the β-SUB2 clone is not fruit-specific and hence is not described further here.

In base pairs 1–2644 of SEQ ID NO:7, the promoter region contains a putative TATA box and DNA motifs with homology to cis-acting sequences that have been shown to be necessary for maximal cell specific expression of reporter genes in pollen of transgenic tobacco plants. These conserved regions known as the LAT56/59 and PB boxes (gaaa/tttGTGA, tGTGGtt, respectively, core motifs in capitals, have been reported within the promoter region of a family of genes expressed during tomato pollen development. Twell D, Yamaguchi J, Wing RA, UshibaJ and McCormick S (1991) Genes and Development 5:496–505. The conserved regions have also been reported in a PG gene family from maize expressed during late pollen development (Alan RL and Lonsdale DM (1992) Plant Mol Biol 20:343–345), and in an exo PG in maize (Barakate A, Martin W, Quigley F and Mache R (1993) J. Mol. Biol 229:797–801). Their presence (core motifs conserved) within the βSUB1 promoter region indicates the fruit β-subunit may also be expressed during tomato pollen development. Three LAT boxes and one PB box (core motifs conserved) have also been identified within 400 bp of the major transcription start site of the tomato fruit PG2 gene.

SEQ ID NO:8 represents the β-subunit coding region, immediately downstream base pair 2645 of SEQ ID NO:7.
βSUB1 promoter GUS plants (Prophetic)

β-subunit mRNA is produced at low levels on a whole tissue basis in non-fruit tissues. For many organs and tissues, this may be explained by a relatively high level of expression restricted to specific tissues, developmental stages or cell layers (e.g. expression in stigma/style tissues or abscission zones). Often the tissues in question are delicate, small or only a few cell layers thick making analysis of developmental and spatial patterns of gene expression impossible by methods such as PCR or northern analysis.

The two most common methods for studying tissue/developmental specific expression in such tissues are in situ hybridizations and use of a reporter gene, such as β-glucuronidase, or GUS. To aid in the analysis of β-subunit expression in fruit and non-fruit tissues wild-type tomato plants will be transformed with βSUB1 promoter:GUS reporter constructions.

The primary objective will be to more precisely define the developmental, spatial and cell/tissue specific expression of each gene during normal growth and development and in response to biotic and abiotic stresses. Special attention will be paid to GUS expression in tissues in which developmentally regulated PGase activities are known to be produced in other systems (i.e. during lateral root initiation, in root caps, during flower development, pollen development, pollen tube growth and abscission zones).

Another reason for utilizing GUS promoter fusions instead of in situ hybridizations is that given what is currently known about the coding sequences of the two genes, the two genes are likely too similar to be distinguished by in situ hybridization. Thus, while the total expression of both genes in a single tissue might be determined by in situ analysis, expression of the individual genes would remain a mystery. Finally, while in situ analysis could currently be used to define floral expression, it is not known where the β-subunit is expressed in leaves and roots and the GUS reporter is superior for "scanning" tissues or developmental stages for expression of a specific gene.

Figure 3:
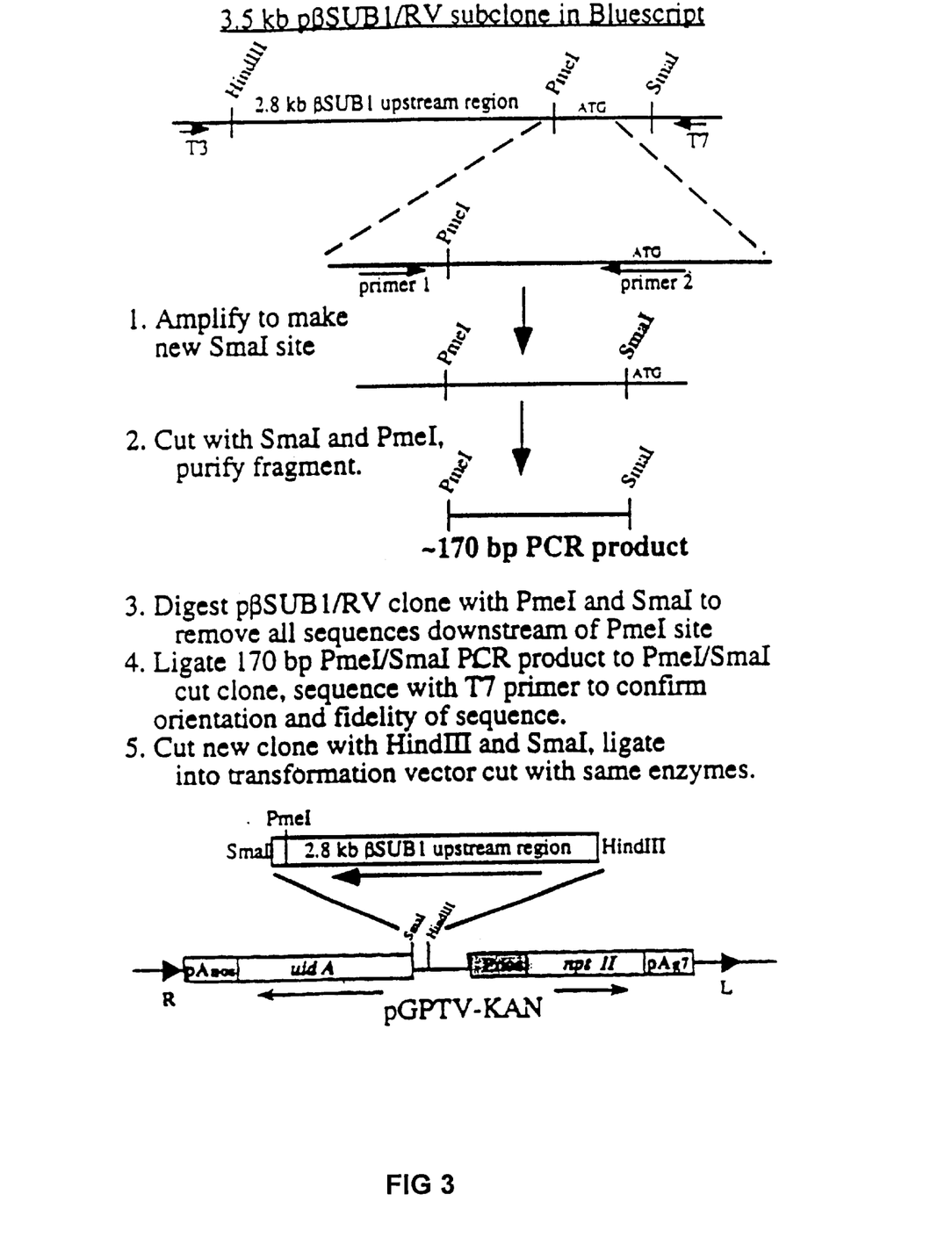
FIG. 3 illustrates a βSUB1:GUS reporter gene construction.

The untranslated leader of βSUB1 does not contain a suitable restriction site to facilitate cloning of the βSUB1 promoter into a plant transformation vector. Therefore, PCR will be utilized to amplify a ~200 bp region immediately 5' to the ATG start codon while simultaneously introducing a unique SmaI site 6 bp 5' of the ATG initiation codon. The location of these primers is illustrated in FIG. 3. The amplified region also contains a unique 8 bp PmeI restriction site at position −142. A 25 bp oligo encompassing the PmeI site and a 30 bp oligo overlapping the ATG initiation codon and containing three base changes to generate the desired Sma I site will be used to amplify this region of the promoter via PCR.

The genomic subclone pβSUB1/RV, a 3.5 kb region containing the promoter and 750 bp of coding region in Bluescript, will be cut with PmeI and SmaI to release a fragment homologous to the amplified promoter region and the remaining downstream βSUB1 coding region (refer to FIG. 3). The PCR amplified promoter fragment will be digested with PmeI and SmaI and ligated into the Pmei/SmaI digested pβSUB1/RV clone containing the remaining (2.7 kb) promoter region. A single sequencing reaction with the T7 primer will confirm the orientation of the cloned insert and fidelity of the PCR reaction in the short amplified region. HindIII and SmaI digestion of this clone will release a 2.85 kb promoter fragment that can be directionally cloned into the plant transformation vector pGPTV-KAN to give a transcriptional fusion with the GUS reporter gene.

The plant binary transformation vector PGPTV-KAN (reported in Becker D, Kemper E, Schell J and Masterson R (1992) *Plant Molec. Biol.* 20:1195–1197), which has the same features as pBIN19 and pBI101 and a β-glucuronidase (uidA) reporter gene located near the right border, will be used. The nptII gene is derived from pRT100neo (as reported in Topfer R, Gronenborn B, Schell J and Steinbiss HH (1980) *Plant Cell* 1:133–139) and therefore lacks the specific point mutation known to reduce NPTII enzyme activity (as reported in Yenofsky RL, Fine M and Pellows JW (1990) *P.N.A.S. USA* 87:3435–3439). Previous vectors used contained this mutation and resulted in some difficulty during antibiotic selection of cotyledons.

βSUB1 promoter:GUS fusions will be introduced into wild type tomato (*Lycopersicon esculentum*, cv. Alisia Craig) using LBA4404 following procedures already established in the lab. We have previously transformed this variety successfully with the sense and antisense β-subunit cDNA constructions. Transformed plants will be selected and regenerated on medium containing 50 mg/L kanamycin. Filatti, J. J., Kiser, J., Rose, B. and Comai, L. (1987) *In Tomato Biotechnology*, eds. Nevins, D. and Jones, R. pp. 199; McCormick, S., Neidermeyer, J., Fry, J., Barnason, A., Horsch, R. and Fraley, R. (1986) *Plant Cell Rep.* 5:81.

As a control, plants will also be transformed with a pGPTV-KAN plasmid lacking a promoter. Ten independent primary transformants for each construction will analyzed by genomic southern analysis to determine gene copy number and verify the structural integrity of the transferred chimeric gene(s). Several independent transformants exhibiting 1) Structurally intact chimeric genes and 2) single or low numbers of insertion events will be selected for further analysis. Single copy insertion events are preferred because the transgenic plants can then easily be selfed and homozygous progeny selected for future experiments.

For βSUB1:GUS primary transformants total protein will be isolated from identically aged developing fruit and assayed quantitatively (using the florigenic substrate 4-MUG) to determine the level of GUS expression in each line. Tissue slices from the same fruit will also be assayed qualitatively for tissue specific expression of the reporter using X-gluc following published procedures (Montgomery et al 1993 and Gallagher, 1992).

Limited amounts of other tissues in addition to fruit can also be analyzed by primary transformants including floral abscission zones, leaf abscission zones, stems and developing flowers. However, because such tissues will be very limiting, homozygous T2 lines will be selected and analyzed more extensively for GUS expression in the tissues described above as well as for expression early in plant development and in root tissues (tissue culture or vermiculite grown seedlings).

Analysis of βSUB1:GUS plants will confirm that expression of the βSUB1 gene is largely fruit specific, with some expression also in flower.

The proposed transcriptional fusion of the βSUB1 promoter region to a GUS reporter gene will help to elucidate the site of tissue and cell specific expression of the fruit β-subunit gene.

The β-subunit promoter of the present invention is highly active in developing tomato fruit from as early as 10 days after pollination up to the onset of ripening, at which time it becomes inactive. Using the promoter to drive the expression of transgenic genes in tomato or other climacteric fruit will allow one to target biochemical and developmental processes of specific interest, in particular, in developing fruit prior to the onset of ripening without affecting gene expression during the ripening process.

By use of the promoter of the present invention, processes relating to sugar or starch metabolism, pathogen resistance, flavor, acidity, color, and the like can be targeted for enhancement during development without affecting such processes during ripening. Those processes will not be affected in other portions of the plant where the processes are necessary for normal plant function. The high degree of specificity afforded by the β-subunit promoter represents a clear advantage over existing promoters available.

We claim:

1. A gene construct comprising a protein encoding nucleotide sequence not natively associated with SEQ ID NO:7 and a sufficient portion of base pairs 1–2644 of SEQ ID NO:7 such that in tomato the portion promotes the tissue specific expression of the protein encoding nucleotide sequence in tomato fruit tissue.

2. A plant cell comprising the gene construct of claim 1.

3. A plant seed comprising the gene construct of claim 1.

4. A gene construct comprising a fruit specific promoter having the DNA sequence of base pairs 1–2644 SEQ ID NO:7 and a protein encoding nucleotide sequence not natively associated with the promoter.

5. A plant cell comprising the gene construct of claim 4.

6. A plant seed comprising the gene construct of claim 4.

* * * * *

```
                         SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
         (A) LENGTH: 10 amino acids
         (B) TYPE: amino acid
         (C) STRANDEDNESS:
         (D) TOPOLOGY: linear (ii) MOLECULE TYPE: peptide (v) FRAGMENT TYPE: internal (vi) ORIGINAL SOURCE:
         (A) ORGANISM: Lycopersicon esculentum (xi) SEQUENCE DESCRIPTION: SEQ ID NO:1:

Asn Gly Asn Gly Ala Asn Gly Gln Xaa Val
1               5                   10

(2) INFORMATION FOR SEQ ID NO:2:

(i) SEQUENCE CHARACTERISTICS:
         (A) LENGTH: 7 amino acids
         (B) TYPE: amino acid
         (C) STRANDEDNESS:
         (D) TOPOLOGY: linear (ii) MOLECULE TYPE: peptide (v) FRAGMENT TYPE: internal (vi) ORIGINAL SOURCE:
         (A) ORGANISM: Lycopersicon esculentum (xi) SEQUENCE DESCRIPTION: SEQ ID NO:2:

Ala Asn Ala Gly Asp Gln Tyr
1               5

(2) INFORMATION FOR SEQ ID NO:3:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "oligonucleotide"

(iii) HYPOTHETICAL: YES (xi) SEQUENCE DESCRIPTION: SEQ ID NO:3:

GGNAAYGGNG CNAAYGG                                                  17

(2) INFORMATION FOR SEQ ID NO:4:

(i) SEQUENCE CHARACTERISTICS:
         (A) LENGTH: 17 base pairs
         (B) TYPE: nucleic acid
         (C) STRANDEDNESS: single
```

(D) TOPOLOGY: linear (ii) MOLECULE TYPE: other nucleic acid
           (A) DESCRIPTION: /desc = "oligonucleotide"

(iii) HYPOTHETICAL: YES (xi) SEQUENCE DESCRIPTION: SEQ ID NO:4:

AAYGCNGGNG AYCARTA                                                         17

(2) INFORMATION FOR SEQ ID NO:5:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "oligonucleotide"

(iii) HYPOTHETICAL: YES (iv) ANTI-SENSE: YES (xi) SEQUENCE DESCRIPTION: SEQ ID NO:5:

ATRTCNCCRC TRTGYTTYTC                                                      20

(2) INFORMATION FOR SEQ ID NO:6:

(i) SEQUENCE CHARACTERISTICS:
           (A) LENGTH: 2191 base pairs
           (B) TYPE: nucleic acid
           (C) STRANDEDNESS: double
           (D) TOPOLOGY: linear (ii) MOLECULE TYPE: cDNA (vi) ORIGINAL SOURCE:
           (A) ORGANISM: Lycopersicon esculentum (xi) SEQUENCE DESCRIPTION: SEQ ID NO:6:

TCTCTCTCTT CATCTCTGTT TCACACCAAA GAAATGCACA CTAAAATTCA TCTTCCTCCC           60

TGCATCTTAC TTCTTCTTCT GTTCTCACTA CCATCTTTCA ATGTTGTTGT AGGTGGAGAT          120

GGTGAATCTG GTAACCCATT TACACCCAAA GGTTATCTGA TTAGGTACTG GAAGAAACAA          180

ATCTCAAATG ACTTACCAAA GCCATGGTTT CTTCTGAACA AGGCATCTCC ATTGAATGCT          240

GCACAATATG CAACTTACAC TAAACTTGTT GCTGATCAAA ATGCACTCAC CACACAGCTC          300

CATACCTTTT GCTCTTCAGC AAATCTCATG TGTGCACCAG ATCTGTCACC AAGTCTTGAA          360

AAACACAGTG GAGATATCCA TTTTGCCACT TACAGTGACA AAAACTTTAC CAATTATGGA          420

ACCAATGAAC CTGGAATTGG AGTTAACACT TTCAAGAACT ACTCTGAAGG AGAAAACATC          480

CCTGTAAATT CTTTCAGGCG ATATGGTAGA GGTTCTCCCC GTGACAATAA ATTTGACAAT          540

TACGCCTCTG ATGGCAATGT TATTGACCAA AGTTTCAATT CCTATAGCAC AAGTACTGCT          600

GGAGGTTCAG GCAAATTCAC AAATTACGCG GCGAATGCCA ATGACCCCAA TCTGCATTTC          660

ACTTCCTATT CCGATCAAGG AACAGGAGGT GTACAGAAAT TCACAATATA CTCACAAGAA          720

GCCAATGCTG GTGACCAGTA TTTCAAAAGT TACGGCAAAA ATGGGAATGG TGCTAATGGT          780

GAATTCGTCA GCTATGGAAA TGACACAAAT GTTATCGGCT CAACATTTAC AAATTATGGT          840

CAGACAGCAA ATGGGGGAGA CCAAAAATTC ACATCTTATG GTTTCAACGG CAATGTTCCT          900

GAAAATCATT TCACCAACTA TGGTGCTGGA GGTAATGGTC CATCTGAAAC TTTTAATAGT          960

-continued

```
TACAGAGATC AATCGAATGT TGGAGATGAC ACATTCACTA CCTATGTTAA GGATGCAAAG    1020

GCGGTGAAGC GAATTTCACC AACTATGGTC AATCATTCAA TGAAGGTACT GATGTATTCA    1080

CTACTTACGG CAAAGGGGGT AATGACCCAC ATATCAATTT CAAAACTTAC GGAGTTAACA    1140

ACACTTTCAA AGATTATGTC AAAGATACTG CTACATTTTC CAATTACCAC AACAAAACTT    1200

CCCAAGTTTT AGCATCGTTG ATGGAGGTCA ACGGTGGTAA AAAGGTGAAT AACCGGTGGG    1260

TTGAGCCCGG AAAGTTTTTC CGGGAGAAGA TGTTGAAGAG TGGTACAATC ATGCCTATGC    1320

CAGATATAAA GGATAAGATG CCTAAAAGGT CCTTTTTGCC CCGGGTGATT GCTTCCAAAT    1380

TACCATTTTC TACTTCAAAA ATTGCTGAGC TGAAGAAAAT CTTCCACGCC GGTGATGAGT    1440

CTCAGGTGGA GAAGATGATC GGCGATGCAT TGAGTGAGTG TGAAAGAGCA CCGAGCGCCG    1500

GTGAGACGAA ACGATGTGTT AATTCAGCTG AAGATATGAT TGATTTCGCA ACATCAGTGT    1560

TGGGTCGAAA CGTCGTCGTT CGAACGACTG AGGATACAAA AGGATCAAAT GGAATATCA     1620

TGATTGGATC AGTCAAAGGA ATCAACGGTG GAAAAGTTAC TAAATCAGTA TCATGTCATC    1680

AAACGCTGTA CCCTTACTTA CTGTATTACT GTCATTCGGT TCCTAAAGTC CGGGTCTACG    1740

AAGCGGATAT TTTGGACCCG AATTCAAAGG TTAAGATCAA TCATGGTGTC GCGATTTGCC    1800

ACGTGGATAC ATCTTCATGG GGACCGAGTC ACGGAGCGTT TGTCGCACTC GGGTCGGGAC    1860

CCGGGAAAAT AGAAGTTTGT CATTGGATCT TTGAGAATGA TATGACTTGG GCAATTGCTG    1920

ATTGAGAAAA AAAAAAGAAA TGAAATAATA TGCAAAATTT CTAATTCGGG TCGAACCGGG    1980

TGTGTTACAA GAAGAAGAAA AAAGGTACCA CTGGTTTGAC TTTTATAGTA ATTATTATTA    2040

TTATAGTCTT AATTTATATT TTGAGTAATT TTCGTGTAAG TTTCTCTTTG CCTTCATTAA    2100

GTATGAATGG CTATCAATTT ACACTATTTG TTATGTAATC ATTTTATTGT TGACTCATAT    2160

TTGAGCAAGG TAATGTAGTT ATTGCCAGAT G                                   2191
```

(2) INFORMATION FOR SEQ ID NO:7:

(i) SEQUENCE CHARACTERISTICS:
        (A) LENGTH: 3231 base pairs
        (B) TYPE: nucleic acid
        (C) STRANDEDNESS: double
        (D) TOPOLOGY: linear     (ii) MOLECULE TYPE: DNA (genomic)

(vi) ORIGINAL SOURCE:
        (A) ORGANISM: Lycopersicon esculentum     (xi) SEQUENCE DESCRIPTION: SEQ ID NO:7:

```
GATATCTCTT TAGAAGCATT ATATTAGTGA ATAATTGTAC AACATTAATT TTTTAACACT      60

CCAAAAAACA AAAGGAGGAG GAGGAAAAAT TCATTTAAAA AAAAAAGTTT GAATAGCGTT     120

AAGATAGCAC TATACTCATA ATTTTCTAAT TAATTCCTCA ATCACAATTA ATTTTAATAA     180

AATAATAAAG TTAAAAAAAT GTATTAATGG GAAGGCCCCT AACCTCAGTG AGCTCTTAAG     240

TCACAAAAAC ATCAACATTT CATTAGATGA CGTACTAGCC GAACTTAAAT TAAATTAAAT     300

TAGTATATAG TATCAATTAT TATCCTCGCT GGAAAAAAAA GGTCCACATG TATATTATTC     360

CTAATAATTA CACATACACT ACACAATTAT TTTTGAAATA GTTGCTTCCT TAGTTAAATT     420

GCTTCACTTA CTTTTTTTTA ATTCATTAAA AGCAATGTTT CTTAGTAACT TTTTAAAACT     480

TTTCATAATA AGTTTAATAC TCAATAACTT AAAAATATTT TAATACATTT GGTATATATT     540

TAATTTTTTT TTTTTGAAAT TCAAAATAAT CCAGCTGCTA CATCTCTATC TTTCAAATAA     600

ATACTCTGCT TATGTTTTCG GAGTATGCAA ACCTAAACAA ATTATATGCT ACCGACTTGA     660
```

| | |
|---|---|
| CTCATCACGC AATGAGGGAG ATTGATCTCG GGCTACTTAT GTAGATGACC ACCTCCTAAA | 720 |
| TTTAAAAAAA TTCATTTGAT TTTTTAAACT TCAATTTATA TCAAATTAAA ATACGTCAAA | 780 |
| TAAATTCTAT GAAAGGAATT CTTTTTAAAA AAAAAAAACA ATCTAGTTTC AAGAATTTAG | 840 |
| TGGCCACTAG AAAGATAAGT GAAAAAGGTA TTACCAATAA AGTCCTTAAA GAGTAGGACA | 900 |
| TATTACAGAT TTTGCCATTG TCACGGGCTT TTGTCTCTGA CTATGAGGTA CAAATGAAAG | 960 |
| TTTTATCATC TTTCACTTAA AATAAAATAA AAAAGTTTTA TATGAGAGAT AAAAAGAGAG | 1020 |
| CAATAATTAA AATAATGGCA CACATGAGAG TATTACTATT TTGAAGAGTG TTTGAGTATC | 1080 |
| ACAAAAAGTT GCATAAAAAA TTCATTACAT AAAACAAAAA CAAAATAAAT AACGCGTTGT | 1140 |
| TCACAATTCA TTTTTGAAAC CAAAAAAAGG TACCACCAAA TGTTCATATT TTACGCGGCT | 1200 |
| TCTATGCCTT ATCTGTCACT AAATTTAGCC TCAACCCCCC CCCCCCCCCA AACAAATAAC | 1260 |
| ATATGCCCTT TTACCACCTC CGAAATAAGA ACTTAACGTG TATTTAAGTT ATATATATCG | 1320 |
| TTGGTATAAA TTTTTTTTAC GTGATTATGT TATTGTTATC TATTATATCA TATTAACATG | 1380 |
| TCATATTTTA TAAAACTTTA GGGGTGTATT TGGTGCAATA ATATTCAGTG AGTTTCGCGG | 1440 |
| TTGCTTATTT TGAAATACGA ATTTCTTTAA CTTTTCTTGA TGTTTGACAA TTAAGTAAAA | 1500 |
| GATTATGAGG GGGGTGTGGG GGATTGGTGG TGGAAGGAAA TAATGAATTT GAAATATCAC | 1560 |
| TTATGAATCT TATTTTTCAA TACAAAGATC ATTTCTTTGT TTTGTTTTTT TAAAGAAGAA | 1620 |
| TTTAATATAG AAAAAAATTAA AAAAGTACTC CATGCCAAAC AAACCCTACA TATTCCACAT | 1680 |
| TTTAAGGAGA CTTACAATTG TACATCTTTT CATAATCTTG TAACATAAAA AAACAATTAT | 1740 |
| ACTATAATTT TCCTTATTCA TTTTTATTCG TCAAATACTT TAAGAAAATA CAATTTATGT | 1800 |
| TCACTTATAA CTTTTAACAT ATTAAAACAT GAACATTAAT TATTATTTCT CAAAAATCAT | 1860 |
| ACAAAATTTA AGTAAACAAG TAAAAGTGAA TCGAATGAAA TATAATAGAA AAAGAAAAAA | 1920 |
| AAAAGAAGTA ACGATGCTTT TATTGCAAGG TAAGGGGCTT GGTTCTTGGT GTGGGGTGGG | 1980 |
| TTGTTCCCAA TGTTGTAATG CCCTAATGTT TAGGGTAGTC CTCTTTTTAA GCCTTTGCTT | 2040 |
| GTCTCAATGA ATACTCTCAA AGAGGTTCAT TAATGTTTTG GAGTTCCCAA AATGCTAATG | 2100 |
| TCCTCTCTTC AAAACTTTCT CATTTTTAAT ATTACTCATT CCTAGAGATT TTTTCTCTCT | 2160 |
| TATAAATGTA AAAATATGAA TTGAAATTTG AAATCTTTAC TTTGAGGGGC TAAAATGTCA | 2220 |
| AGCCAAATTA TAGAACAAAC AACTTGGAGT AATTTTTTTA AAAAAATATG AGTGGTCCAC | 2280 |
| ATCAGAAAGC AGATATAAAC AAAGCAAAAG CTCTCTGCTT ACACTATTGA AGTAGAAAAT | 2340 |
| AGTATTTGTT TCACCTTAAT CAGAGATCTT ATGCTCATCT GCTAATTTTA TTGAGAGTGT | 2400 |
| TACTTTCAAA TGGACTTTAT AATTCGCGAT TTAAATTTAG GTTCGGACTA AGTAGTGATA | 2460 |
| AACAGTGTTT AAACCTGAAA GGGGCAAAGA ACTAACCCCA CACTCCATCA TCTTCTCTAT | 2520 |
| TTTCTACTAT ACTCTTTTAG AACCTTCTAC TATAAATTAT GTGCCTCCAA CCAAACCTCC | 2580 |
| CTACCAACAT TCTACTCTTC ACCTTCACCT TTCTCTCTCT TCATCTCTGT TTCACACCAA | 2640 |
| AGAAATGCAC ACTAAAATTC ATCTTCCTCC CTGCATCTTA CTTCTTCTTC TGTTCTCACT | 2700 |
| ACCATCTTTC AATGTAAGTA ACAATCTTCA ACTCATCTAT TTCAACTTCT TGTACAAAGA | 2760 |
| TTGTACCTTT ATATGTACCC ATTAAGTATT CTTGATTTTT GTCATAATAA TTGTAGCTTT | 2820 |
| TATGTACCTT ACTAAGTGTC AAATAAAGTA ACTTTGATTT TATCTAAAGA TTGTACTCAT | 2880 |
| GGGGTTAGGT GTCATATGAA GTAAATCTTG ATTTTGTTAC AAAGATTGTA ACTTTATGCA | 2940 |
| GTTTTGGTGT CAATGCAGGT TGTTGTAGGT GGAGATGGTG AATCTGGTAA CCCATTTACA | 3000 |

-continued

```
CCCAAAGGTT ATCTGATTAG GTACTGGAAG AAACAAATCT CAAATGACTT ACCAAAGCCA    3060

TGGTTTCTTC TGAACAAGGC ATCTCCATTG AATGCTGCAC AATATGCAAC TTACACTAAA    3120

CTTGTTGCTG ATCAAAATGC ACTCACCACA CAGCTCCATA CCTTTTGCTC TTCAGCAAAT    3180

CTCATGTGTG CACCAGATCT GTCACCAAGT CTTGAAAAAC ACAGTGGAGA T             3231
```

(2) INFORMATION FOR SEQ ID NO:8:

(i) SEQUENCE CHARACTERISTICS:
        (A) LENGTH: 587 base pairs
        (B) TYPE: nucleic acid
        (C) STRANDEDNESS: double
        (D) TOPOLOGY: linear     (ii) MOLECULE TYPE: cDNA     (vi) ORIGINAL SOURCE:
        (A) ORGANISM: Lycopersicon esculentum     (xi) SEQUENCE DESCRIPTION: SEQ ID NO:8:

```
ATGCACACTA AAATTCATCT TCCTCCCTGC ATCTTACTTC TTCTTCTGTT CTCACTACCA      60

TCTTTCAATG TAAGTAACAA TCTTCAACTC ATCTATTTCA ACTTCTTGTA CAAAGATTGT     120

ACCTTTATAT GTACCCATTA AGTATTCTTG ATTTTTGTCA TAATAATTGT AGCTTTTATG     180

TACCTTACTA AGTGTCAAAT AAAGTAACTT TGATTTTATC TAAAGATTGT ACTCATGGGG     240

TTAGGTGTCA TATGAAGTAA ATCTTGATTT TGTTACAAAG ATTGTAACTT TATGCAGTTT     300

TGGTGTCAAT GCAGGTTGTT GTAGGTGGAG ATGGTGAATC TGGTAACCCA TTTACACCCA     360

AAGGTTATCT GATTAGGTAC TGGAAGAAAC AAATCTCAAA TGACTTACCA AAGCCATGGT     420

TTCTTCTGAA CAAGGCATCT CCATTGAATG CTGCACAATA TGCAACTTAC ACTAAACTTG     480

TTGCTGATCA AAATGCACTC ACCACACAGC TCCATACCTT TTGCTCTTCA GCAAATCTCA     540

TGTGTGCACC AGATCTGTCA CCAAGTCTTG AAAAACACAG TGGAGAT                   587
```